(12) United States Patent
Colobert et al.

(10) Patent No.: US 11,430,110 B2
(45) Date of Patent: Aug. 30, 2022

(54) RADIOGRAPHIC IMAGING METHOD, RADIOGRAPHIC IMAGE PROCESSING DEVICE, AND RADIOGRAPHIC IMAGING DEVICE

(71) Applicant: PROTEOR, Saint-Apollinaire (FR)

(72) Inventors: Briac Colobert, Dijon (FR);
Jean-Charles Gesbert, Saint Malo de Phily (FR); Vincent Carre, Saint Apollinaire (FR)

(73) Assignee: PROTEOR, Saint-Apollinaire (FR)

( * ) Notice: Subject to any disclaimer, the term of this patent is extended or adjusted under 35 U.S.C. 154(b) by 132 days.

(21) Appl. No.: 16/753,148

(22) PCT Filed: Oct. 1, 2018

(86) PCT No.: PCT/FR2018/052406
§ 371 (c)(1),
(2) Date: Apr. 2, 2020

(87) PCT Pub. No.: WO2019/069001
PCT Pub. Date: Apr. 11, 2019

(65) Prior Publication Data
US 2020/0320687 A1 Oct. 8, 2020

(30) Foreign Application Priority Data
Oct. 3, 2017 (FR) ..................... 17 59209

(51) Int. Cl.
*G06T 7/00* (2017.01)
*G06T 7/70* (2017.01)
*G06T 7/55* (2017.01)
*A61B 6/00* (2006.01)

(52) U.S. Cl.
CPC ............ *G06T 7/0012* (2013.01); *A61B 6/466* (2013.01); *A61B 6/5247* (2013.01); *A61B 6/56* (2013.01); *G06T 7/55* (2017.01); *G06T 7/70* (2017.01); *A61B 6/4417* (2013.01); *A61B 6/505* (2013.01);
(Continued)

(58) Field of Classification Search
CPC ....... A61B 6/4417; A61B 6/466; A61B 6/505; A61B 6/5247; A61B 6/56; G06T 7/0012; G06T 7/55; G06T 7/70; G06T 2207/10116; G06T 2207/30004; G06T 2207/30204
See application file for complete search history.

(56) References Cited

U.S. PATENT DOCUMENTS 7,639,866 B2 * 12/2009 Pomero .................. G06T 17/00
382/128

FOREIGN PATENT DOCUMENTS

EP 2323101 A2 8/2011

OTHER PUBLICATIONS

Gesbert, J., "Modelisation 3D du rachis scoliotique fusion de donnees et personnalisation experimentale", 2014, 163 pages, XP055487234.
(Continued)

*Primary Examiner* — Mark R Gaworecki
(74) *Attorney, Agent, or Firm* — Sughrue Mion, PLLC (57) ABSTRACT

A method for the radiographic imaging of a three-dimensional internal structure which forms part of an object located within a field of view, a radiographic image processing device and a radiographic imaging device, which are particularly suitable for locating a characteristic point of an internal structure on a radiographic image.

20 Claims, 3 Drawing Sheets

(52) U.S. Cl.
CPC ............ *G06T 2207/10116* (2013.01); *G06T 2207/30004* (2013.01); *G06T 2207/30204* (2013.01)

(56) References Cited

OTHER PUBLICATIONS

Campbell-Kyureghyan, et al., "The prediction of lumbar spine geometry: method development and validation", 2005, 10 pages total, XP027795127.

International Search Report (PCT/ISA/210) dated Feb. 5, 2019, issued by the International Searching Authority in counterpart International Patent Application No. PCT/FR2018/052406.

* cited by examiner

RADIOGRAPHIC IMAGING METHOD, RADIOGRAPHIC IMAGE PROCESSING DEVICE, AND RADIOGRAPHIC IMAGING DEVICE

This application is a National Stage of International Application No. PCT/FR2018/052406 filed Oct. 1, 2018 claiming priority from French Patent Application No. 17 59209 filed on Oct. 3, 2017, the entire disclosures of which are incorporated herein by reference.

The invention relates to a method for the radiographic imaging of a three-dimensional internal structure which forms part of an object located within a field of view, a radiographic image processing device and a radiographic imaging device.

Particularly, the imaging method according to the invention is suitable for locating a characteristic point of an internal structure on a radiographic image.

In one embodiment, the imaging method according to the invention is also suitable for calculating a three-dimensional model of an object to be imaged in a field of view.

Radiographic imaging methods for three-dimensional reconstruction are known. By way of example, French patent application FR-A-2 810 769 describes a method wherein the three-dimensional shape of a model representing the object is calculated using a previously known generic model of the object. The user must manually locate on each of the two radiographed images control markers belonging to said object, which may be points, segments, lines, arcs, contours, edges or others, which requires simultaneously from him precise anatomical knowledge for locating the control markers accurately, time and a high level of precision. After this location, a geometric position of each marker is determined in a three-dimensional frame of reference, then used to calculate the shape of the model using the known generic model. This significant human intervention in terms of manual location on the radiographs particularly limits reconstruction reproducibility when carried out by personnel who are not highly specialized.

There exist imaging methods seeking to limit specialist intervention. This is the case of the method described in the document FR-A 2 856 170. The method described uses a confinement volume of the object, estimated using a geometric pattern visible on two images, and the position of the source. It uses a geometric model comprising information suitable for establishing, via an estimator of the object a geometric characteristic for the model representing the object.

The method described has the drawback of calculating the three-dimensional shape of the model using points obtained only by processing radiographic images. In the event of incorrect point identification, the model is falsified.

The aim of the present invention is particularly that of providing a reliable method wherein specialist intervention is limited. In particular, one aim of the invention is that of facilitating and enhancing the identification of internal anatomical structures on a two-dimensional radiograph. A further aim is that of proposing a reliable and accurate method for the three-dimensional reconstruction imaging of an object.

For this purpose, the invention firstly relates to a method for the radiographic imaging of a three-dimensional internal structure which forms part of an object located within a field of view.

According to the invention, the method comprises:
a) receiving first image data generated in a three-dimensional reference frame of reference, representative of at least one two-dimensional radiographic image of the internal structure of the object,
b) receiving second image data generated in the reference frame of reference, representative of a three-dimensional image of an outer boundary of the object,
c) estimating from the second image data the coordinates in the reference frame of reference of first characteristic markers of the internal structure, and, optionally, the value of at least one characteristic parameter of the internal structure,
d) calculating, in the reference frame of reference, the three-dimensional shape of a model representing said internal structure from a previously known generic model of said internal structure, this generic model including points corresponding to the first markers, the calculated model being obtained by deformation of the generic model such that said calculated model observes a shape that is closest possible to an isometry of the generic model while keeping the points of the deformed generic model coincident with the first markers, and optionally by applying to the calculated model the characteristic parameter(s) of the internal structure,
e) selecting at least one second characteristic marker of the internal structure to be located on the radiographic image, and for each second marker:
i) identifying a point belonging to the model calculated in step d) corresponding to the second marker,
(ii) calculating the coordinates of a projection of this point onto the radiographic image,
iii) determining from the first image data the coordinates of the second marker on the radiographic image by searching for same in a search zone located around the coordinates of the projection.

The object mentioned above may comprise particularly a patient's spine, pelvis, or knee, or more generally consist of all or part of the patient's body. In these different cases, the internal structures to be viewed may consist particularly of the patient's bones contained in the field of view.

The marker(s) mentioned above are anatomical markers which may be points, segments, lines, arcs, contours, edges or others, or more generally consist of any characteristic anatomical point or element of the patient's skeleton. Optionally, the first and second markers may be the same markers.

The characteristic parameter(s) of the internal structure may be anatomical parameters of the internal structure, such as for example anatomical marker dimensions. By way of example, waist girth or the height separating girth at armpit level are morphological dimensions (measurable on the outer boundary) suitable for estimating an anatomical dimension of the internal structure (hip width, vertebral height).

The method according to the invention enables less, or even no, intervention of an operator to locate the anatomical points (second markers) on a two-dimensional radiograph, thus facilitating this location and rendering same more reliable. This is obtained thanks to the estimation of the geometric position of the first markers using the data from the three-dimensional digital image of the outer boundary, this estimation being suitable for adapting a previously known generic model of the internal structure to be viewed, which subsequently serves to locate the second markers on a radiographed image. Thus, the search for markers on the 2D (two-dimensional) radiographs is initiated by the 3D (three-dimensional) digitization of the outer boundary of the object. This limits the risks of incorrect identification of the markers on the radiographs. These points are indeed searched in limited search zones, defined around projections of the markers on a calculated model and are not defined merely by radiographic image processing.

In other words, the location of the second markers on the radiographic images uses a 3D digitized image of the object, processed to correct an existing generic model. The projection of this corrected model makes it possible to determine a probable position of the second markers on a two-dimensional radiograph. Processing the radiographic image around each probable position probable also makes it possible to locate the second markers reliably. Thus, this image processing requires fewer resources as it is performed in a restricted zone of the radiographic image.

It shall be noted that step c) is carried out before step (d), step (b) is carried out before step (c) and that step (a) may be carried out at any time before step (e).

The first and second image data are for example data representative of the coordinates of the points of a 2D or 3D image. They may consist of an electrical signal (image signal).

The second image data received in step (b) may be generated by an imaging system comprising at least one optical sensor. These second image data may advantageously be generated by means of one or a plurality of optical sensors, particularly non-irradiant or ionizing, for example one or a plurality of optical image sensors, converting a light signal into an electrical signal. The light signal used may be visible or not. By way of example, an imaging system suitable for measuring an optical depth is usable, for example of the type described in the document WO 2007/043036.

In one embodiment, during step (c), the estimated geometric position of the plurality of first markers may be determined by carrying out first of all the determination (c)(i) of the coordinates of external markers positioned on the outer boundary in a three-dimensional frame of reference, then the estimation (c)(ii) of the coordinates of the first markers in the same frame of reference using external markers.

Step (c)(i) may be obtained by calculating by means of at least one mathematical model, or by processing the second image data, these external markers being marked on the outer boundary. It shall be understood that this marking is carried out before the generation of the second image data received in step (b).

The manual marking used in cases of image data processing may be passive marking. It may consist of positioning external markers drawn or attached on the patient's skin, exhibiting for example a particular shape and/or a color or having a reflective surface suitable for reflecting a light flash.

The drawn or attached external markers may be located manually, for example designated on the 3D digitized image by an operator, or automatically for example by image processing software suitable for differentiating colors, light intensities, etc. Human intervention is required in this case, but remains limited.

The marking may also be active marking, such as the positioning of transmitters on the patient's skin, such transmitters being optionally capable of transmitting a characteristic signal of the position thereof capable of being detected by the imaging system suitable for digitizing the outer boundary. This signal, for example a light signal, in the visible range or not, may be specific to each marker and/or be transmitted occasionally at known time intervals or for a known duration. Human intervention is then limited to the positioning of the markers on the patient.

Step (c)(ii) may particularly be carried out by calculation by means of a mathematical model. It is understood that no human intervention is then required when step (c)(i) also uses a mathematical model, enhancing location reproducibility. By way of example, a model may be used suitable for locating internal markers (belonging to the internal structure) using the outer boundary.

The imaging method according to the invention is thus suitable for locating reliably and quasi-automatically markers on one or a plurality of radiographic images.

The first image data received in step (a) may be generated by scanning by moving at least one radioactive source in a translation direction non-parallel with an image capture direction.

As a general rule, the second markers are preferably chosen among markers to be located on each of the two radiographic images (also referred to as stereo-correspondent), and optionally among markers to be located on a single radiographic image (also referred to as non-stereo-correspondent).

In one particular embodiment, during step (a), first image data representative of two radiographic images recorded along two non-parallel image capture directions are received.

The reception of first image data representative of two radiographic images captured along two non-parallel image capture directions may be used for the three-dimensional reproduction of the internal structure of an object.

For this purpose, during step (e), the second markers are chosen among the second (stereo-correspondent) markers to be located on each of the two radiographic images, and, optionally among the second (non-stereo-correspondent) markers to be located on a single radiographic image. The method then further comprises:

f) calculating the coordinates of the second markers in the reference frame of reference using the coordinates thereof on at least one of the radiographic images determined in step (e), g) correcting the model calculated in step (d) by coinciding the points of the calculated model corresponding to the second markers with the coordinates of those calculated in step (f).

The model calculated using a previously known generic model of the internal structure is thus established in a first phase to locate the second markers of the object (step (e) (iii)) on one or on both radiographs, then is merely corrected to obtain a reliable three-dimensional model of the internal structure.

The use of second stereo-correspondent, that is to say visible on both radiographed images, markers makes it possible to enhance the quality of the corrected model. The quality of the corrected model may further be enhanced using further second non-stereo-correspondent markers. The number of second markers suitable for use for correcting the model may be chosen according to the nature of the internal structure to be imaged. By way of example, for a vertebra, the use of some ten markers may suffice. In general, from 10 to 100 control markers shall be used.

Advantageously, in one embodiment, the first image data received in step (a) are generated simultaneously, by scanning, by moving in synchronism, in the same translation direction non-parallel with the image capture directions, two radioactive sources emitting two ionizing ray beams respectively in the two image capture directions. This may help generate radiographic image data in the same three-dimensional frame of reference, for example after suitable calibration of the radioactive sources.

In one embodiment, the first image data and the second image data are generated simultaneously. The first and second image data may then be generated in the same three-dimensional frame of reference, for example after suitable calibration of the image recording device. This makes it possible to avoid carrying out a realignment of the various images in the same three-dimensional frame of reference and to simplify the use of the method according to the invention. This frame of reference may then serve as a reference frame of reference for the method according to the invention.

In a further embodiment, the first image data and the second image data may be generated in different three-dimensional frames of reference. In other words, each image or each type of image is recorded in a three-dimensional frame of reference which is specific thereto. This is for example the case when the images are generated at separate times. In this case, at least one of the receiving steps (a) and (b) comprises a step of transforming the image data received to the reference frame of reference.

This transformation step may for example by carried out by means of a transformation matrix which makes it possible to switch from one frame of reference to another. This transformation matrix may be determined such that common elements to the first image data and the second image coincide in the reference frame of reference selected. These common elements may form part of the image such as, for example, the contour of the images or be radio-opaque marking elements of known dimensions positioned on the object to be imaged before the generation of the image data.

Thus, as a general rule, the first image data may be generated in a first three-dimensional frame of reference, the second image data may be generated in a second three-dimensional frame of reference. In one alternative embodiment, the first and second three-dimensional frames of reference may be a single frame of reference, for example a single reference frame of reference. In a further alternative embodiment, the first and second three-dimensional frames of reference may be different frames of reference. In the latter case, at least one of the receiving steps (a) and (b) comprises a step of transforming the image data received to express the first and second image data in the same reference frame of reference, which may correspond to one of the first and second frames of reference or which may be a further frame of reference selected as a reference.

The imaging method according to the invention may further comprise a step of data transmission, particularly to a display device. These data may be:
first and/or second image data, suitable for viewing on a screen the radiographic/3D image(s);
data representative of the coordinates of the first markers,
data representative of the coordinates of each second marker determined in step (e)iii), which makes it possible to view on a screen the position of the second markers, particularly on the radiographic image(s), and,
if applicable, data representative of the corrected model calculated in step (g), which makes it possible to view a 3D reconstruction of the internal structure.

The visualization of the 3D reconstruction may be separate from the other views.

There is also proposed a device for processing radiographic images comprising means arranged to carry out the steps of the imaging method according to the invention.

In particular, the device for processing radiographic images comprises:
means for receiving image data for receiving first image data generated in a three-dimensional frame of reference representative of at least one two-dimensional radiographic image of the internal structure of the object, and second image data generated in a three-dimension frame of reference representative of a three-dimensional image of an outer boundary of the object processing means connected to the receiving means arranged to carry out at least steps c) to e) described above of the method according to the invention, optionally transmission means, particularly to a display device.

This image processing device may comprise or be integrated in one or a plurality of processors, for example microcontrollers, microprocessors or others.

The receiving means are for example an input port, an input pin, a wireless connection device (for example using "Bluetooth", "Near Field Communication" or "WIFI" technology) or other. The processing means may for example comprise a processor core or CPU (Central Processing Unit). The transmission means may for example comprise an output port, an output pin, a wireless connection device (for example using "Bluetooth", "Near Field Communication" or "WIFI" technology) or other.

The processing means may also be arranged to carry out steps (f) and (g) described above.

The image processing device may also comprise storage means connected to the processing means.

There is also proposed a device for the radiographic imaging of a three-dimensional internal structure which forms part of an object comprising:
a first radiographic imaging system arranged to capture at least one two-dimensional radiographic image of the internal structure of the object by means of at least one radioactive source and to generate in a three-dimensional frame of reference first image data representative of the radiographic image captured,
a second imaging system comprising at least one optical sensor, arranged to capture a three-dimensional image of an outer boundary of the object and to generate in a three-dimensional frame of reference second image data representative of this image,
the radiographic image processing device according to the invention connected to the first and second imaging systems for receiving the first and second image data.

There is further proposed a computer program product comprising instructions or code segments for executing the steps of the imaging method described above when these instructions are executed by a radiographic image processing device, particularly that of the invention, comprising particularly a processor. This program may for example be stored on a storage medium of the hard drive, downloaded, or other type.

Further features and advantages of the invention will emerge in the course of the following description of one of the embodiments thereof, given by way of non-limiting example, with reference to the appended drawings, wherein.

Figure 1:
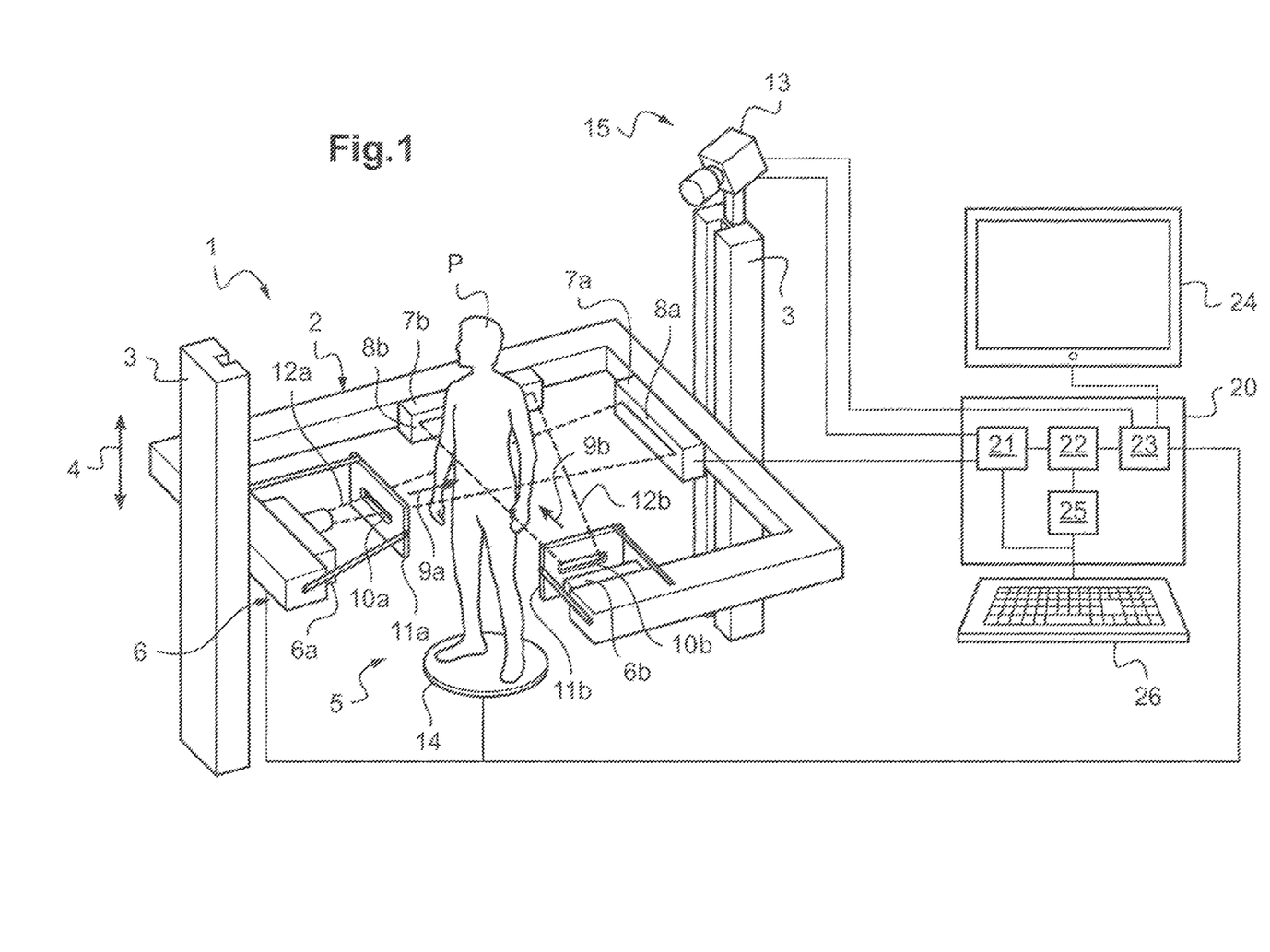
FIG. 1 is a schematic view of a radiographic imaging device according to one embodiment of the invention, suitable for carrying out a front image capture and a side image capture by radiography of the patient and for carrying out 3D digitization of the outer boundary of the patient.
Figure 2:
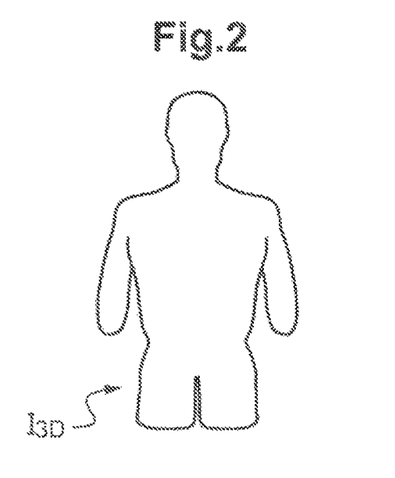
FIG. 2 is a schematic representation of a 3D digitized image of the outer boundary of the patient.

FIG. 1 represents a radiographic imaging device 1, particularly for the three-dimensional reconstruction, including a movable frame 2 suitable for moving vertically in a motorized manner along vertical guides 3, in a translation direction 4.

This frame surrounds a field of view 5 wherein a patient P may take position, for example upright, which makes it possible to view the position of the bones of this patient's skeleton in the upright stance, which may be important for example for patients suffering from scoliosis. Obviously, the patient could be in a seated position if required.

The movable frame 2 bears a first radioactive source 6a and a second radioactive source 6b. Each radioactive source 6a, 6b is associated with a detector 7a, 7b, respectively which is disposed facing the source 6a, 6b, beyond the field of view 5. Each detector 7a, 7b comprises at least one horizontal row 8a, 8b of detection cells. The sources 6a, 6b and the detectors 7a, 7b form part of a first radiographic imaging system 6.

The radioactive sources 6a, 6b are suitable for emitting ionizing rays, particularly X-rays, in the image capture directions 9a, 9b respectively, these ionizing rays being suitable for being detected by the detectors 7a, 7b. The image capture direction 9a is anteroposterior in relation to the patient P whereas the image capture direction 9b is lateral in relation to the patient P.

Conventionally, the ionizing rays emitted by the sources 6a, 6b each pass through a horizontal slot 10a, 10b formed in a reticle 11a, 11b such as a metallic plate, to generate a horizontal beam 12a, 12b of ionizing rays in the field of view 5.

Obviously, the radioactive sources and the detectors may be greater than 2 in number, and the image capture directions of these different radioactive sources may, if needed, not be perpendicular with one another, or even horizontal.

The device further comprises at least one optical sensor 13 for carrying the external digitization of the patient P. Any type of optical image sensor is usable, such as CCD (Couple Charge Device) and CMOS (Complementary Metal Oxide Semiconductor) sensors or sensors capable of measuring an optical depth. Note however that it is preferable to use an optical sensor having a high precision and mesh resolution.

In the example, this optical sensor 13 is mounted on one of the vertical guides 3. The patient is further upright on a platform 14 that may be rotated by means of a motor. A 3D image of patient may thus be captured by rotating the platform 14 over 360°. This 3D image could be captured by positioning a plurality of optical sensors 13 around the patient P instead of rotating the patient. 5 or 6 optical sensors distributed around the patient could for example be used to digitize the outer boundary of the patient P, particularly simultaneously with the capture of the radiographs. In a further alternative embodiment, the 3D image could be captured by moving a single optical sensor 13 around the patient, either manually, or automatically by means of a motorized arm, a rail, or other.

The optical sensor(s) 13 form part of a second imaging system 15.

The two detectors 7a, 7b and the optical sensor 13 are connected to a radiographic image processing device 20, for example a microcomputer or other electronic control system such as, for example one or a plurality of microprocessor, microcontroller or other type processors.

The microcomputer 20 comprises means for executing a computer program suitable for carrying out the method described in the present invention. It thus comprises image data receiving means 21 for receiving image data representative of one or a plurality of radiographic images and a three-dimensional image of an outer boundary of the object. It also comprises processing means 22 connected to the receiving means 21 arranged to execute steps (c) to (g) described above of the method according to the invention. Finally, it comprises transmission means 23, particularly to a display device 24, herein a screen, connected to the processing means 22. It may also comprise storage means 25 connected to the processing means 22, which may be random access memory or RAM memory, an EEPROM (Electrically-Erasable Programmable Read-Only Memory), or other. These storage means may particularly store the various models and data, and optionally the computer program.

The microcomputer 20 is further herein equipped with: an input interface comprising at least one keyboard 26 and generally a mouse (not shown), and an output interface comprising at least the screen 24 and generally a printer (not shown).

The microcontroller 20 may also be connected to the motorized drive means (not shown) contained in the guides 3 and in the rotating platform 14, to the sources 6a, 6b and to the optical sensor 13, so as to control, on one hand, the vertical movement of the frame 2 and the emission of the ionizing rays and, on the other, the rotation of the rotating platform 14 and the operation of the optical sensor 13.

The detectors 7a, 7b may for example be gaseous detectors sensitive to low radiation doses, for example of the type described in the documents FR-A-2 749 402 or FR-A-2 754 068. Obviously, further types of detectors could optionally be used within the scope of the present invention. Detection may be carried out by a purely linear detector (one image line at a time), or by a matrix detector of any aspect ratio.

The operation of the device described above is now detailed with reference to FIGS. 2 to 8.

By means of the microcomputer 20, two digital radiographic images I2Da, I2Db of the patient P are captured, for example by scanning the field of view 5 with ionizing ray beams 12a, 12b along a height corresponding to the height of the zone of the patient to be viewed, for example the spine or pelvis, or even the whole skeleton. For this purpose, the frame 2 is preferably suitable for moving along a sufficient height, for example of 70 cm or more, or of 1 meter or more. Following suitable calibration of the sources 6a, 6b and the detectors 7a, 7b, the radiographic imaging system 6 generates first image data of the two radiographs in the same three-dimensional frame of reference.

Before or after the capture of the digital radiographic images, again by means of the microcomputer 20, a three-dimensional digital image I3D (FIG. 2) of the outer boundary of the patient P is captured by rotating, particularly over 360°, the platform 14 supporting the patient P. The second imaging system 15 then generates second image data in a second three-dimensional frame of reference different to the preceding one, the image captures not being capable of being simultaneous. It is then necessary to transform the first or the second image data in order to express the same in the same reference frame of reference, which may be one of the frames of reference wherein the first or second image data are generated or another frame of reference. This transformation may be carried out (by the processing means 22) by means of a transformation matrix as described above. For a simultaneous capture of this 3D digital image with the radiographs, instead of using a rotating platform, a plurality of optical sensors 13 disposed around the patient P could be used. Suitable calibration of the sources 6a, 6b and of the optical sensor 13 would then make it possible to generate the first and second image data in a same three-dimensional frame of reference.

Figure 5:
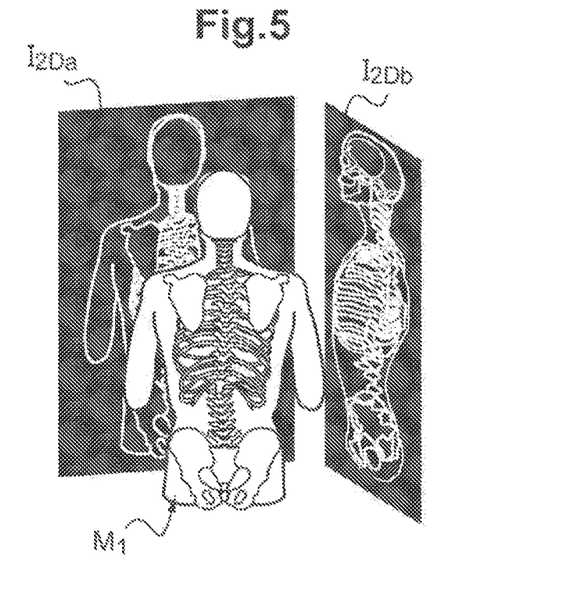
FIG. 5 is a schematic representation of a calculated 3D model of the patient's skeleton and of the projections thereof on the radiographic images.

The digital images I2Da, I2Db, I3D of the examined part of the patient are transmitted to the processing means 22. They may optionally be recorded in the memory of the microcomputer 20 and viewed on the screen 24 of the microcomputer. In the example, the digital radiographic images I2Da, I2Db are anteroposterior and lateral images (FIG. 5).

There is then estimated a geometric position in the 3D reference frame of reference of one or a plurality of points of interest (first markers) belonging to the internal structure. These first markers are characteristic of the internal structure.

This estimation preferably involves estimating the geometric position of external markers, in other words markers forming part of the outer boundary. The location of external markers on the outer boundary of the object has the advantage of enabling estimation without radiation of the internal structure of this object.

The estimation of the geometric position of the external markers is preferably automatic, for example using known methods, such as those described by Michonski et al. (Automatic recognition of surface landmarks of anatomical structures of back and posture. J Biomed Opt. 2012 May; 17(5):056015).

Gaussian curves may also be used to identify external markers which may subsequently be used to estimate the position of the first internal markers.

Figure 3:
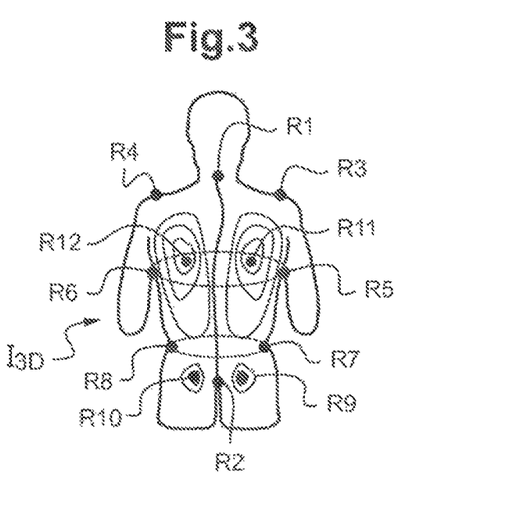
FIG. 3 is a similar representation to FIG. 2 wherein external markers are represented.

As represented in FIG. 3, the following external markers may be preferentially identified:

R1: C7 vertebra prominens, R2: top of gluteal fold, R3 and R4: left and right shoulders (points immediately vertical to the subaxillary folds), R5 and R6: left and right subaxillary folds, R7, R8: left and right points of the waist, R9, R10: left and right posterior superior iliac spines, R11, R12 inferior angles of the left and right scapula.

Anatomical parameters such as the dimensions of the vertebrae and bone structures may be estimated with regression equations linked with external anthropometric measurements, as described for example by Bertrand et al., Estimation of external and internal human body dimensions from few external measurements, Journal of Musculoskeletal Research, Vol. 12, No. 4 (2009) 191-204). Such an estimation of the characteristic lengths of anatomical markers of the internal structure makes it possible to calculate the possible position of this internal marker (herein referred to as first marker).

A number of studies have also proposed external-internal correlations for estimating the centers of vertebral bodies using the external surface (The prediction of lumbar spine geometry: method development and validation. Campbell-Kyureghyan N, Jorgensen M, Burr D, Marras W. Clin Biomech (Bristol, Avon). 2005 June; 20(5):455-64).

Various non-rigid transformation laws may also be envisaged to estimate the position of the markers of the internal structure (Seo et al. An automatic modeling of human bodies from sizing parameters. In: SI3D'03: Proceedings of the 2003 symposium on Interactive 3D graphics, New York, N.Y., USA, ACM Press (2003) 19-26).

The method is described herein with reference to the spinal column, but a similar method could also be used for a single internal structure of which prior knowledge is available, such as a single bone, such as a single vertebra, a ligamental structure, or other, or a set of anatomical structures such as a lower or upper limb, or others. Further anatomical markers suitable for the structures to be viewed/imaged will then be used. Furthermore, according to the internal structure to be viewed/imaged, the digitization of the outer boundary may be carried out on the patient's whole body or on a restricted part of the body (only the back of the torso for example).

Once the coordinates (in the reference frame of reference) of the first markers are estimated and the values of the anatomical parameters have optionally been estimated, it is possible to calculate the three-dimensional shape of a model representing the internal structure using a generic model thereof.

For this purpose, generic models of the internal structures represented in the radiographic images are used, in particular the vertebrae, but optionally also further internal anatomical structures, such as ligaments or others. These models may be recorded in the microcomputer 20.

A generic model, for example established using a database, may be defined as a mesh of some hundred to some hundred thousand points of a structure.

Such generic models are for example established using databases containing data relating to particular markers of the structure. These data may comprise positions of characteristic points of the structure, characteristic lengths of the structure, or characteristic segments, lines or arcs of the structure, and/or contours and edges of the structure. For a vertebra, the base contains for example some twenty characteristic points of the vertebra, characteristic lengths of the vertebra.

The database may also contain data relating to the relative location of the internal structure in the skeleton of the subject from whom it originates. In the case of a vertebra, this consists for example of the angular orientation of the vertebra and the curvature of the spine at the level of the vertebra.

It is possible to categorize the objects in different categories so as to distinguish between the characteristic data of healthy subjects or those with a condition, and/or characteristic of the weight, height, age or any other type of parameter of a subject.

A generic model may comprise for example statistical data (means, variances, etc.) for each parameter of the database, or mathematical equations suitable for determining for a given object the location of characteristic points using the value of estimating parameters of this object.

In one embodiment, the three-dimensional shape of a model representing the internal structure is calculated using a generic model thereof for example by configuring the latter by means of the first markers and optionally the anatomical parameters that have been estimated, preferably automatically, using the digital image I3D of the outer boundary.

Figure 4:
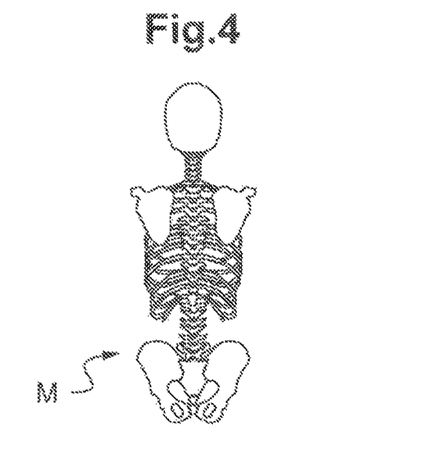
FIG. 4 is a schematic representation of a 3D generic model of a skeleton.

FIG. 4 represents schematically the generic model M of the subject's bone structure, FIG. 5 showing the calculated model M1 obtained by configuring the model M. The scoliosis of the subject viewed is thus visible on the calculated model M1.

This configuration of the generic model M may be carried out by modifying the dimensions of the generic model according to the anatomical parameters.

It is possible for example to use the method described by Hwang et al. ("Rapid Development of Diverse Human Body Models for Crash Simulations through Mesh Morphing," SAE Technical Paper 2016-01-1491, 2016).

For this, the coordinates of one or a plurality of points of the generic model M corresponding to first markers are made to correspond with the coordinates of these first markers estimated using the data of the image I3D. This positioning may be carried out in relation to the positions of the vertebrae associated with each pair of ribs. Then, the generic model is deformed geometrically retaining the lengths to correspond to the constraints given by the outer boundary. A mechanical model may also be used in this step (Closkey, R. F., Schultz, A. B. and Luchies, C. W. (1992) A model for studies of the deformable rib cage. Journal of Biomechanics, 25, 529-539).

Figure 6A:
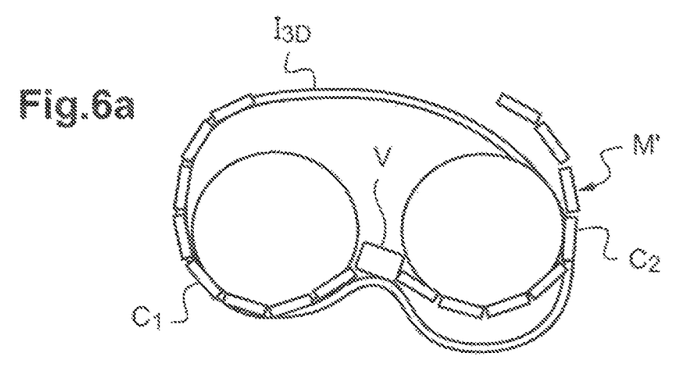
FIGS. 6a and 6b are schematic transversal cross-sectional representations showing the deformations of the 3D model.
Figure 6B:
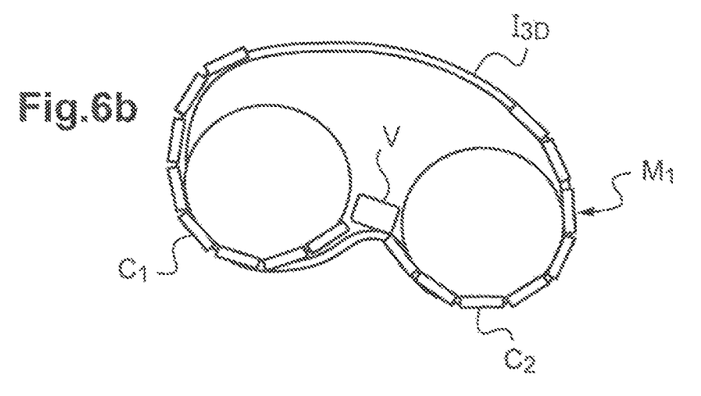

For example, when the structure to be imaged is the rib cage, the generic model M is firstly set to the patient's dimensions by means of the first markers and the anatomical parameters to obtain a model M', then, it is positioned inside the digitized image I3D of the outer boundary in relation to the positions of the vertebrae associated with each pair of ribs, as represented in FIG. 6a. The model M' is then in the same reference frame of reference as the image I3D of the outer boundary. In this FIG. 6a, the letter "V" denotes a vertebra, to which the ribs C1 and C2 are connected. The solid line corresponds to the image of the outer boundary I3D, whereas the dotted lines correspond to the model M'. The ribs C1, C2 of the model M' are then deformed geometrically retaining the lengths thereof to correspond to the constraints given by the outer shape of the torso, in particular gibbosities of the rib cage, as represented in FIG. 6b. There is thus obtained a calculated 3D model M1 of the internal structure to be viewed/imaged. During this step, rigging (deformation of the skeleton by direct or inverse kinematics) and skinning (association of each bone of the skeleton with a portion of the skin) animation techniques may be used (Avatar reshaping and automatic rigging using a deformable model. Feng A., Casas D., Shapiro A., Proceeding MIG'15 Proceedings of the 8th ACM SIGGRAPH Conference on Motion in Games p 57-64).

The projection of the calculated 3D model M1 on each of the radiographed images I2Da, I2Db (FIG. 5) is subsequently carried out. This projection makes it possible to locate anatomical markers (second markers) in the 2D radiographs without requiring image processing, which makes it possible to accelerate this location and render same more reliable. The choice of the second markers may be automatic or manual with operator designation. These second markers may be the same as the first markers or not.

Figure 7:
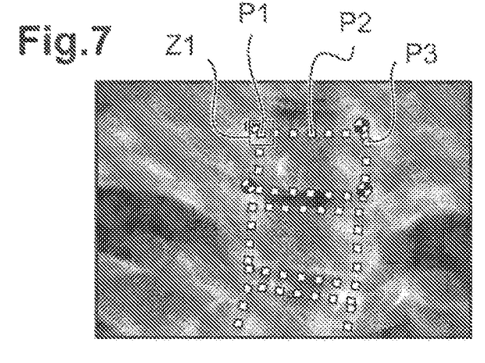
FIG. 7 represents the projections of the points on a radiograph and a search zone.

The projection used is for example a linear projection. This projection may be carried out using the DLT (acronym of "Direct Linear Transformation") technique. It is also possible to modify the equations of the DLT technique by performing a simplification. By projecting the model M1, there are obtained the estimated 2D coordinates of the second markers in each radiographed image I2Da, I2Db. This initial estimation is subsequently refined (step (e)(iii)), by defining a search zone situated around the projection of the second marker of the calculated model in the radiographed image. FIG. 7 represents the projections of a plurality of these points Pi on a radiograph, where i is an integer representing a number of points. For clarity reasons, only some points P1, P2, P3 are represented. The zone Z1 corresponds to the search zone of the projection marker P1.

This step commences for example with ROI (Region of Interest) segmentation.

It is then possible to apply filters suitable for locating high negative and positive density zones (oriented filter). A Canny filter applied to these ROIs subsequently makes it possible to determine contours which may be used with the generalized Hough transform technique (using a vertebra model).

Alternatively, instead of using oriented and Canny filters, the initial estimations may be enhanced automatically with an active contour method such as gradient vector flow (GVF) (Moura et al., Fast 3D reconstruction of the spine from biplanar radiographs using a deformable articulated model. Med Eng Phys. 2011 October; 33(8):924-33).

Figure 8:
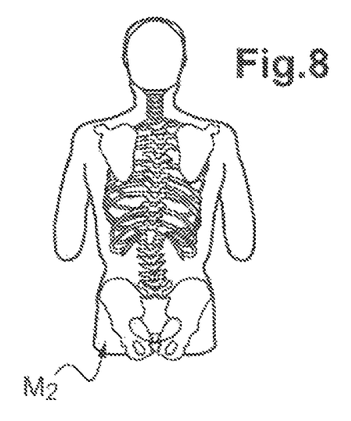
FIG. 8 represents a reconstructed 3D model of the patient's skeleton.

When the 2D projections of the 3D model M1 have been optimized by processing the radiographic data, the 3D model M1 may be reconstructed. For this purpose, the model M1 is corrected for example by Direct Linear Transformation (DLT) using the same pairs of points (with the updated coordinates thereof) as for the projection (second markers). A reconstructed model M2 is then obtained (FIG. 8).

This reconstruction is carried out using second markers which are stereo-correspondent. The epipolar geometry, using non-stereo-correspondent markers, may also be used for obtaining a more accurate reconstruction of the model M2 (NSCP (Non-Stereo-Correspondent Point) type method). For example, after the reconstruction of the stereo-correspondent points, the model M2 is initialized. The non-stereo-correspondent points of the model M2 will be projected only in one of the two radiographic views (I2Da or ID2b) wherein it is known that the search will be possible. The model M2 is updated by integrating the non-stereo-correspondent points.

The present invention thus makes it possible to reconstruct an accurate 3D model of an internal structure by limiting the dose of radiation emitted to the field of view.

The invention claimed is:

1. A method for radiographic imaging of a three-dimensional internal structure which forms part of an object located within a field of view, the method comprising:
   a) receiving first image data generated in a three-dimensional reference frame of reference, representative of at least one two-dimensional radiographic image of the internal structure of the object,
   b) receiving second image data generated in the reference frame of reference, representative of a three-dimensional image of an outer boundary of the object,
   c) estimating from the second image data coordinates in the reference frame of reference of first characteristic markers of the internal structure,
   d) calculating, in the reference frame of reference, the three-dimensional shape of a model representing said internal structure from a previously known generic model of said internal structure, this generic model including points corresponding to the first markers, the calculated model being obtained by deformation of the generic model such that said calculated model observes a shape that is closest possible to an isometry of the generic model while keeping the points of the deformed generic model coincident with the first markers,
   e) selecting at least one second characteristic marker of the internal structure to be located on the radiographic image, and for each second marker:
   i) identifying a point belonging to the model calculated in step d) corresponding to the second marker,
   (ii) calculating the coordinates of a projection of this point onto the radiographic image,
   iii) determining using the first image data the coordinates of the second marker on the radiographic image by searching for same in a search zone located around the coordinates of the projection.

2. The imaging method according to claim 1, wherein, the second image data received in step b) are generated by an imaging system comprising at least one optical sensor.

3. The imaging method according to claim 1, wherein, step c) comprises:
  (i) determining the coordinates of external markers positioned on the outer boundary in the reference frame of reference, obtained:
  by calculating by means of a mathematical model, or
  by processing the second image data, these external markers being marked on the outer boundary,
  (ii) estimating the coordinates of the first markers in the same frame of reference using the external markers.

4. The imaging method according to claim 1, wherein, the first image data received in step (a) are generated by scanning by moving at least one radioactive source in a translation direction non-parallel with an image capture direction.

5. The imaging method according to claim 1, wherein, during step a), first image data representative of two radiographic images recorded along two non-parallel image capture directions are received.

6. The imaging method according to claim 5, wherein, during step e), the second markers are chosen among the second markers to be located on each of the two radiographic images,
  the method further comprising:
  f) calculating the coordinates of the second markers in the reference frame of reference from the coordinates thereof on at least one of the radiographic images determined in step e),
  g) correcting the model calculated in step d) by coinciding the points of the calculated model corresponding to the second markers with the coordinates of those calculated in step f).

7. The imaging method according to claim 6, wherein the first image data received in step a) are generated simultaneously, by scanning, by moving in synchronism, in the same translation direction non-parallel with the image capture directions, two radioactive sources emitting two ionizing ray beams respectively in the two image capture directions.

8. The imaging method according to claim 6, wherein, during step e), the second markers are chosen among the second markers to be located on each of the two radiographic images and from the second markers to be located on a single radiographic image.

9. The imaging method according to claim 1, wherein the first image data and the second image data are generated simultaneously in the same three-dimensional frame of reference.

10. The imaging method according to any claim 1 further comprising:
  a step of transmission, to a display device, of data chosen among the first image data, the second image data, data representative of the coordinates of the first markers, data representative of the coordinates of each second marker determined in step e)iii).

11. The imaging method according to claim 10, wherein the step of transmission include data representative of the corrected model calculated in step g).

12. A radiographic image processing device (20) comprising:
  means (21) for receiving image data for receiving first image data generated in a three-dimensional frame of reference, representative of at least one two-dimensional radiographic image of the internal structure of the object, and second image data generated in a three-dimension frame of reference representative of a three-dimensional image of an outer boundary of the object, and
  processing means (22) connected to the receiving means arranged to carry out at least steps c) to e) of the method according to claim 1.

13. A device (1) for the radiographic imaging of a three-dimensional internal structure which forms part of an object comprising:
  a first radiographic imaging system (6) arranged to capture at least one two-dimensional radiographic image of the internal structure of the object by means of at least one radioactive source (6a, 6b) and to generate in a three-dimensional frame of reference first image data representative of the radiographic image captured,
  a second imaging system (15) comprising at least one optical sensor (13), arranged to capture a three-dimensional image of an outer boundary of the object and to generate in a three-dimensional frame of reference second image data representative of this image,
  the radiographic image processing device (20) according to claim 12 connected to the first and second imaging systems for receiving the first and second image data.

14. The radiographic image processing device of claim 12, further comprising transmission means to a display device.

15. A non-transitory computer readable medium comprising program code segments for executing the steps of the imaging method according to claim 1, when said program is executed by a radiographic image processing device (20).

16. The imaging method according to claim 1, wherein, the step c) of estimating from the second image data coordinates in the reference frame of reference of first characteristic markers of the internal structure further comprises estimating a value of at least one characteristic parameter of the internal structure.

17. The imaging method according to claim 16, wherein in step d), the calculated model is obtained by deformation of the generic model such that said calculated model observes a shape that is closest possible to an isometry of the generic model while keeping the points of the deformed generic model coincident with the first markers, and by applying to the calculated model the at least one characteristic parameter of the internal structure.

18. A method for radiographic imaging of a three-dimensional internal structure which forms part of an object located within a field of view, the method comprising:
  a) receiving first image data generated in a three-dimensional frame of reference, representative of at least one two-dimensional radiographic image of the internal structure of the object,
  b) receiving second image data generated in a further three-dimensional reference frame of reference, representative of a three-dimensional image of an outer boundary of the object,
  wherein at least one of the receiving steps (a) and (b) comprises a step of transforming the image data received to express the first and second image data in the same reference frame of reference,
  c) estimating from the second image data the coordinates in the reference frame of reference of first characteristic markers of the internal structure,
  d) calculating, in the reference frame of reference, the three-dimensional shape of a model representing said internal structure from a previously known generic model of said internal structure, this generic model including points corresponding to the first markers, the calculated model being obtained by deformation of the generic model such that said calculated model observes a shape that is closest possible to an isometry of the generic model while keeping the points of the deformed generic model coincident with the first markers, e) selecting at least one second characteristic marker of the internal structure to be located on the radiographic image, and for each second marker:
i) identifying a point belonging to the model calculated in step d) corresponding to the second marker,
(ii) calculating the coordinates of a projection of this point onto the radiographic image,
iii) determining using the first image data the coordinates of the second marker on the radiographic image by searching for same in a search zone located around the coordinates of the projection.

19. The imaging method according to claim 18, wherein the step c) of estimating from the second image data the coordinates in the reference frame of reference of first characteristic markers of the internal structure further comprises estimating a value of at least one characteristic parameter of the internal structure.

20. The imaging method according to claim 19, wherein in step d) the calculated model is obtained by deformation of the generic model such that said calculated model observes a shape that is closest possible to an isometry of the generic model while keeping the points of the deformed generic model coincident with the first markers, and by applying to the calculated model the at least one characteristic parameter of the internal structure.

* * * * *